(12) United States Patent
Perrey et al.

(10) Patent No.: US 10,398,411 B2
(45) Date of Patent: Sep. 3, 2019

(54) AUTOMATIC ALIGNMENT OF ULTRASOUND VOLUMES

(71) Applicant: General Electric Company, Schenectady, NY (US)

(72) Inventors: Christian Fritz Perrey, Mondsee (AT); Daniel John Buckton, Salzburg (AT); Nitin Singhal, Bangalore (IN); Kajoli Banerjee Krishnan, Bangalore (IN)

(73) Assignee: General Electric Company, Schenectady, NY (US)

( * ) Notice: Subject to any disclaimer, the term of this patent is extended or adjusted under 35 U.S.C. 154(b) by 793 days.

(21) Appl. No.: 15/048,528

(22) Filed: Feb. 19, 2016

(65) Prior Publication Data

US 2017/0238904 A1    Aug. 24, 2017

(51) Int. Cl.
| | |
|---|---|
| *A61B 8/00* | (2006.01) |
| *A61B 8/14* | (2006.01) |
| *A61B 8/08* | (2006.01) |
| *G06T 19/00* | (2011.01) |
| *G06T 7/33* | (2017.01) |

(52) U.S. Cl.
CPC ............ *A61B 8/463* (2013.01); *A61B 8/0883* (2013.01); *A61B 8/145* (2013.01); *A61B 8/465* (2013.01); *A61B 8/466* (2013.01); *A61B 8/469* (2013.01); *A61B 8/483* (2013.01); *A61B 8/5253* (2013.01); *G06T 7/344* (2017.01); *G06T 19/00* (2013.01); *G06T 2200/04* (2013.01); *G06T 2207/10136* (2013.01); *G06T 2207/30048* (2013.01); *G06T 2210/41* (2013.01)

(58) Field of Classification Search
CPC ....... A61B 8/463; A61B 8/0883; A61B 8/465; A61B 8/5253; A61B 8/145; A61B 8/466; A61B 8/483; A61B 8/469; G06T 7/344; G06T 19/00; G06T 2210/41; G06T 2200/04; G06T 2207/30048; G06T 2207/10136
See application file for complete search history.

(56) References Cited

U.S. PATENT DOCUMENTS 8,073,215 B2    12/2011  Lu et al.
2008/0069436 A1  3/2008  Orderud
(Continued)

FOREIGN PATENT DOCUMENTS

| JP | 2013-123582 A | 6/2013 |
|---|---|---|
| WO | 2014039935 A1 | 3/2014 |

OTHER PUBLICATIONS

Lu, X. et al., "AutoMPR: Automatic detection of standard planes in 3D echocardiography," 5th IEEE International Symposium on Biomedical Imaging: From Nano to Macro (ISBI 2008), May 14, 2008, Paris, France, 4 pages.

(Continued)

*Primary Examiner* — Joel Lamprecht
(74) *Attorney, Agent, or Firm* — McCoy Russell LLP

(57) ABSTRACT

Embodiments for aligning a volume to a standard alignment are provided. One example method of aligning a volume constructed from captured image data to a standard orientation includes determining an orientation and a scale of the volume based on a comparison of a volume model representing the volume to captured image data of the volume over time and adjusting the volume according to the determined orientation and scale.

28 Claims, 5 Drawing Sheets

(56) References Cited

U.S. PATENT DOCUMENTS

| | | |
|---|---|---|
| 2009/0238404 A1 | 9/2009 | Orderud et al. |
| 2012/0065510 A1 | 3/2012 | Snare et al. |
| 2015/0190112 A1 | 7/2015 | Yeo et al. |
| 2016/0283687 A1* | 9/2016 | Kamen .............. A61B 5/04028 |
| 2017/0185740 A1* | 6/2017 | Seegerer .............. G09B 23/288 |

OTHER PUBLICATIONS

Orderud, F. et al., "Automatic Alignment of Standard Views in 3D Echocardiograms Using Real-time Tracking," Proc. SPIE 7265, Medical Imaging 2009: Ultrasonic Imaging and Signal Processing, Feb. 7, 2009, Lake Buena Vista, Florida, 7 pages.

Yeo, L. et al., "Fetal Intelligent Navigation Echocardiography (FINE): a novel method for rapid, simple, and automatic examination of the fetal heart," Ultrasound in Obstetrics & Gynecology, vol. 42, No. 3, Sep. 2013, 17 pages.

Machine Translation and Notification of Reason for Refusal issued in connection with corresponding KR Application No. 10-2017-0019840 dated Sep. 21, 2018.

* cited by examiner

AUTOMATIC ALIGNMENT OF ULTRASOUND VOLUMES

FIELD

Embodiments of the subject matter disclosed herein relate to an ultrasound system, for example.

BACKGROUND

During an ultrasound imaging session, 3D/4D volumes may be acquired in order to enable viewing of desired anatomical features that may be obstructed or otherwise difficult to view in traditional 2D imaging. After generating a 3D volume of a desired anatomy, the volume may be aligned to a standard alignment to facilitate location of the desired anatomical features. However, such alignment procedures may be time consuming and may require a high level of experience with ultrasound imaging techniques and the anatomy being imaged.

BRIEF DESCRIPTION

In one embodiment, a method of aligning a volume constructed from captured image data to a standard orientation comprises determining an orientation and a scale of the volume based on a comparison of a volume model representing the volume to captured image data of the volume over time and adjusting the volume according to the determined orientation and scale.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of aligning a volume to a standard orientation. The volume may be generated from a plurality of frames of image data captured via a suitable imaging apparatus, such as an ultrasound imaging apparatus or magnetic resonance imaging apparatus. In one example, the volume may represent an anatomical structure, such as a heart. In order to obtain diagnostically-relevant planes of the volume for display to a clinician (e.g. four chamber view, left ventricular outflow tract etc.), the volume is typically initially oriented to a standard orientation. While alignment of an imaged heart of an adult patient may be relatively easy, due to the patient assuming a standard orientation during imaging, alignment of a fetal heart may be particularly challenging due to the changing and unknown orientation of the fetus during imaging. Previous fetal heart alignment strategies relied on identification of an anatomical feature outside the heart that is easy to identify and orient, such as the fetal spine. However, the spine is not necessarily in the same position relative to the heart in all fetuses. To compensate for the differing anatomies among fetuses, tomographic ultrasound imaging (TUI) may be used during heart alignment with respect to the spine. TUI provides nine views of a slice of a target region of the fetus, thus requiring numerous steps of rotation and translation of the volume, necessitating that the operator have a high level of understanding of the alignment routine and anatomy of the fetus.

According to embodiments disclosed herein, to reduce the manual interaction effort, the volume may be semi-automatically aligned to a standard orientation. As described in more detail below, the semi-automatic alignment process may include user input to only one slice of the volume, namely the four chamber view. The only user interaction is to identify certain landmarks in the four chamber view (e.g., the interventricular septum, crux, and/or apex). Based on this information, an initial position of the heart and the scaling of the heart are determined. In a subsequent step the heart is aligned to a standard orientation by using deformable models, which will be described in more detail below. Standard alignment of the imaged volume (e.g., a heart) may facilitate further diagnostics, including the identification of diagnostically-relevant image planes of the heart, calculation of blood flow/pumping rates, or other suitable diagnostics.

Figure 1:
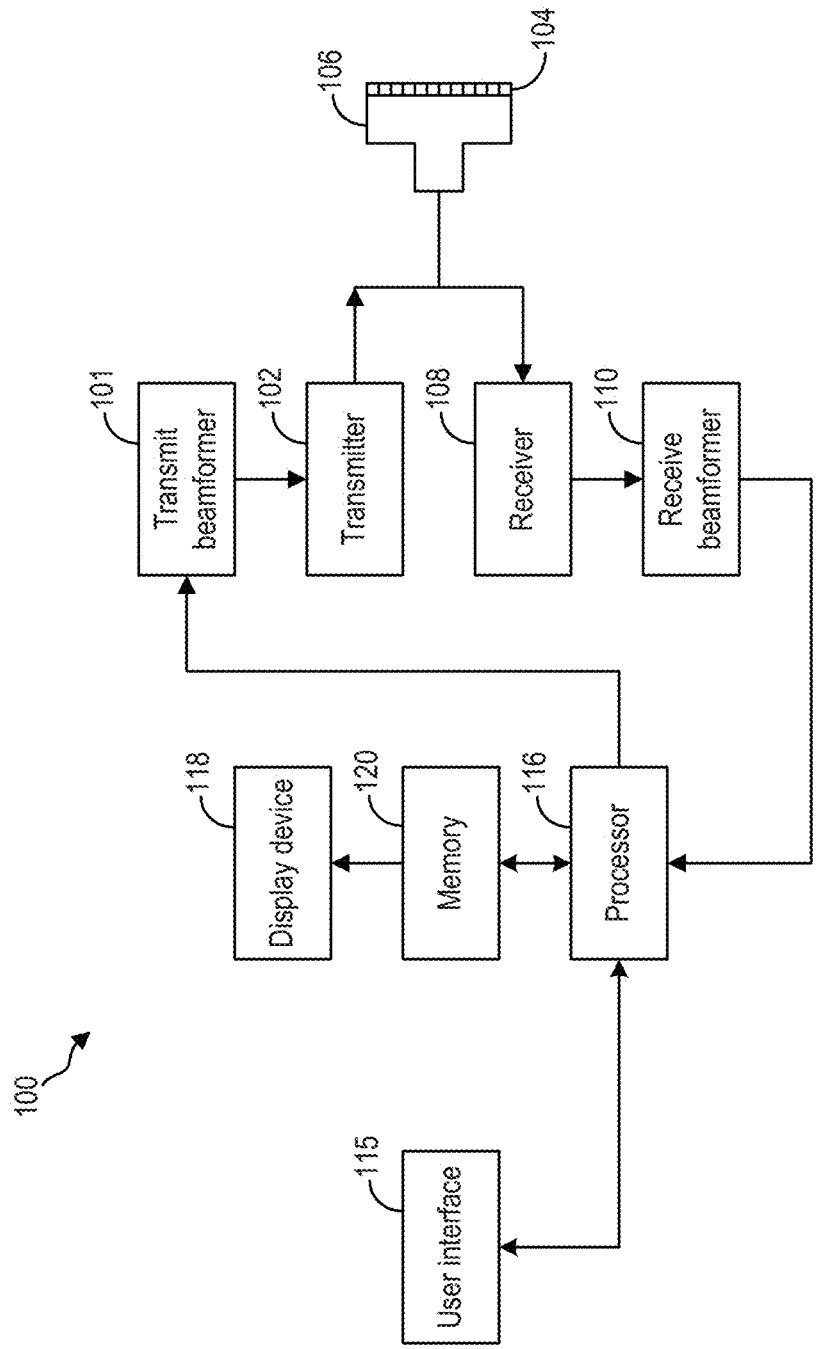
FIG. 1 shows an example ultrasonic imaging system.
Figure 2:
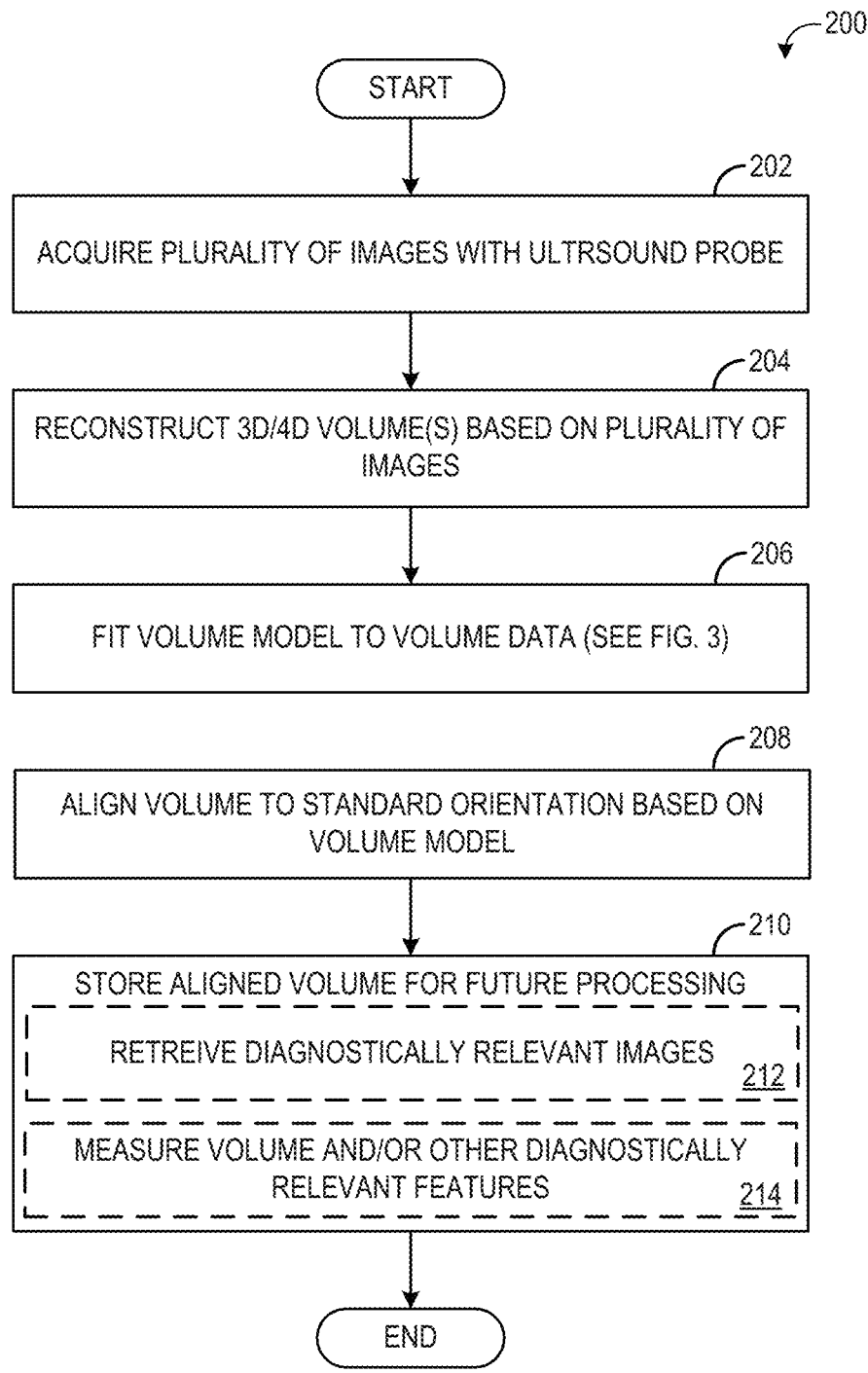
FIG. 2 shows a flow chart illustrating an example method for aligning a volume generated from captured image data to a standard orientation based on a volume model representing the volume.
Figure 3:
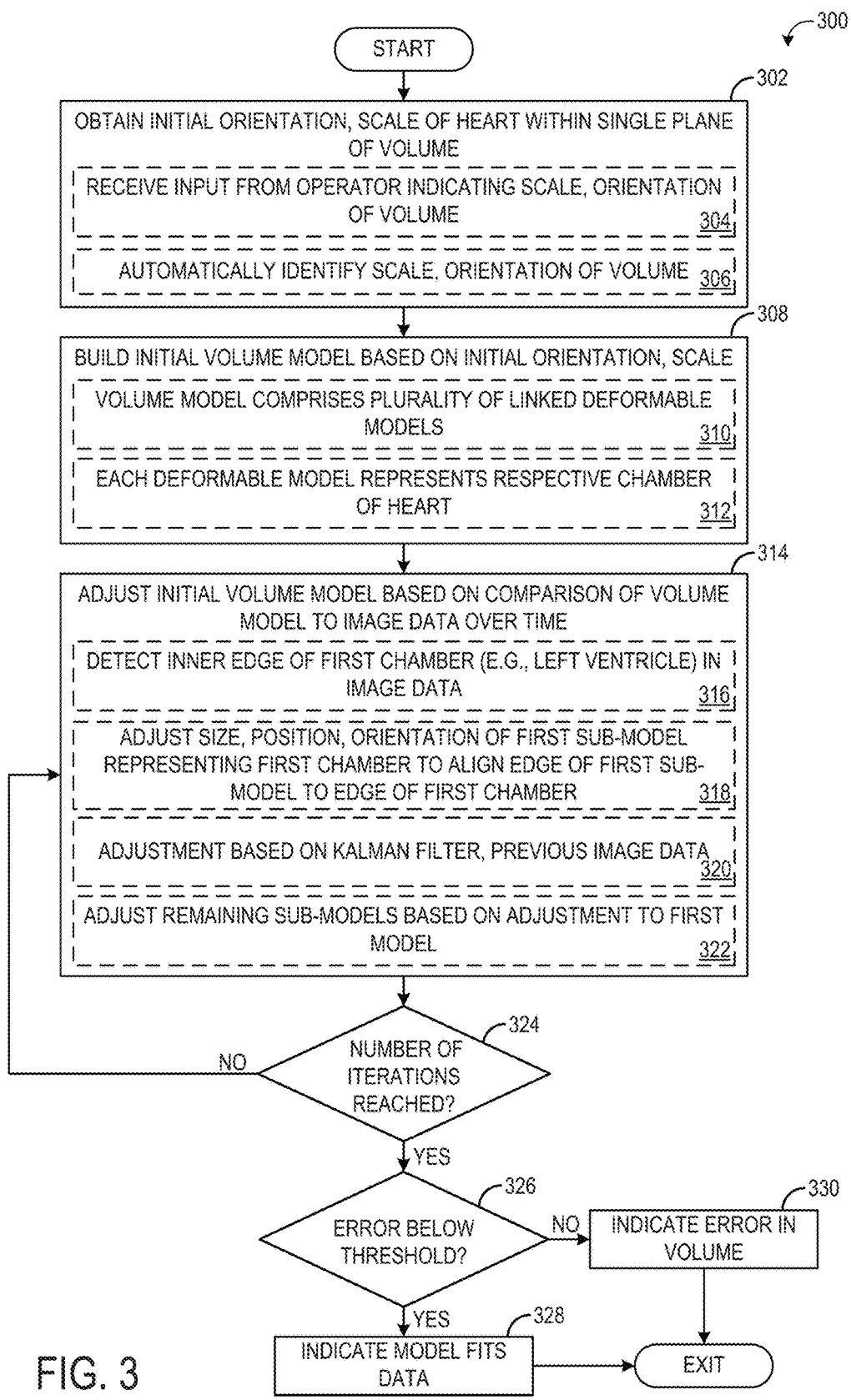
FIG. 3 shows a flow chart illustrating an example method for fitting a volume model to a volume.
Figure 4:
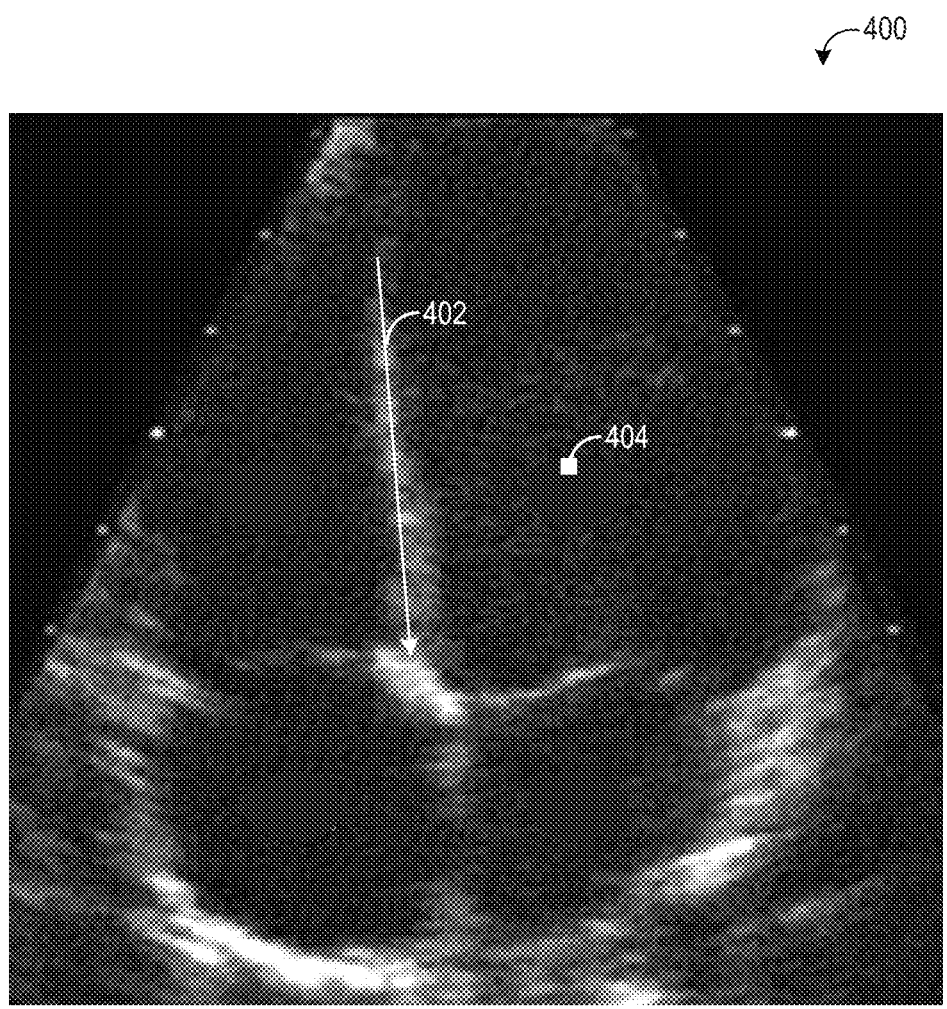
FIGS. 4-6 are example graphical user interfaces that may be output during execution of the method of FIG. 3.
Figure 5:
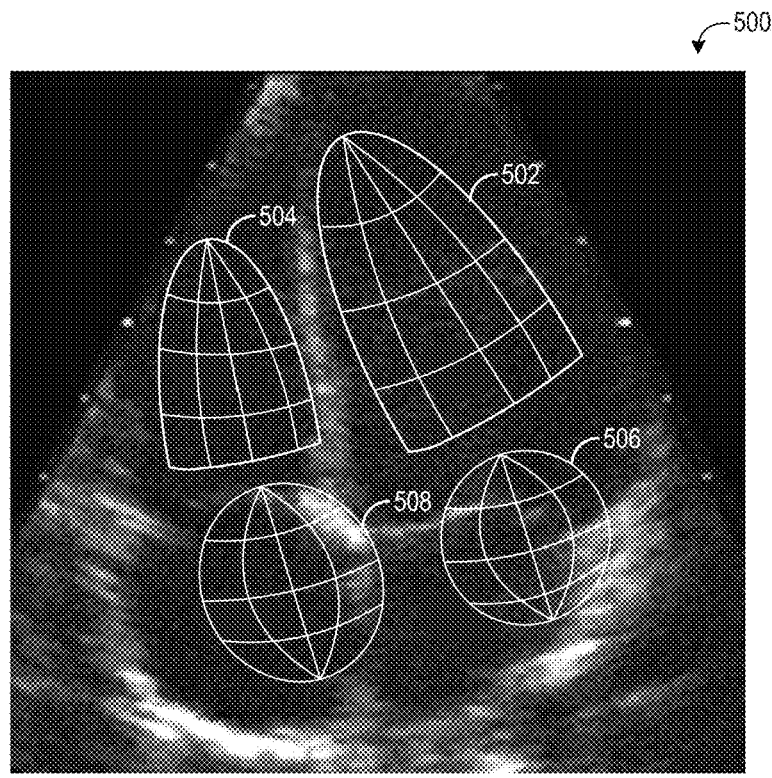
Figure 6:
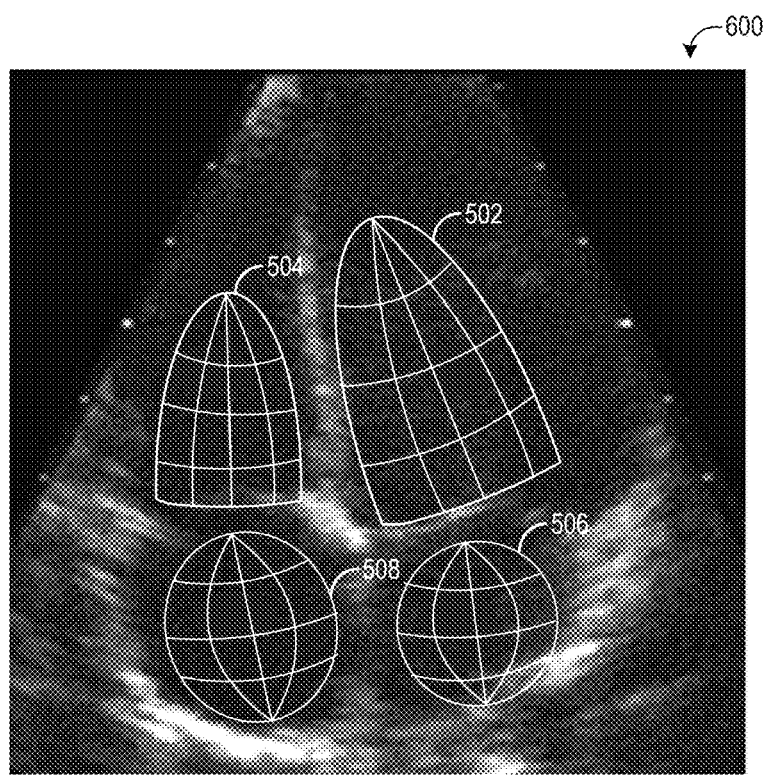

FIG. 1 shows an ultrasound system that may be used to acquire the images for reconstructing a three- or four-dimensional volume of a target region, such as a heart. The ultrasound system of FIG. 1 also includes a computing system including instructions to carry out one or more alignment routines to provide an automatic alignment of the volume. FIGS. 2-3 are flow charts illustrating methods that may be carried out by the computing system of the ultrasound system of FIG. 1. FIGS. 4-6 are example graphical user interfaces that may be displayed during the execution of the methods of FIGS. 2-3.

FIG. 1 is a schematic diagram of an ultrasound imaging system 100 in accordance with an embodiment of the invention. The ultrasound imaging system 100 includes a transmit beamformer 101 and a transmitter 102 that drive transducer elements 104 within a probe 106 to emit pulsed ultrasonic signals into a body (not shown). A variety of geometries of probes and transducer elements may be used. The pulsed ultrasonic signals are back-scattered from structures in the body, such as blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system.

A user interface 115 may be used to control operation of the ultrasound imaging system 100, including controlling the input of patient data, changing a scanning or display parameter, and the like. The user interface 115 may include a graphical user interface configured for display on a display device 118. The graphical user interface may include information to be output to a user (such as ultrasound images, patient data, etc.) and may also include menus or other elements through which a user may enter input to the computing system. In examples described in more detail below with respect to FIGS. 2-3, the user interface may receive inputs from a user indicating, for example, the initial scale and orientation of an anatomical feature within an image displayed via the graphical user interface. The user interface 115 may include one or more of the following: a rotary, a mouse, a keyboard, a trackball, a touch-sensitive display, hard keys linked to specific actions, soft keys that may be configured to control different functions, and a graphical user interface.

The ultrasound imaging system 100 also includes a processor 116 to control the transmit beamformer 101, the transmitter 102, the receiver 108, and the receive beamformer 110. The processor 116 is in electronic communication with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain.

The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image beams and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in the memory 120, from which the images are read and displayed.

As described above, the ultrasound imaging system of FIG. 1 may acquire a plurality of images and construct a three-dimensional volume representing an imaged target region. For example, a fast 3D-sweep acquisition or a spatio-temporal image correlation (STIC) acquisition process may be used to acquire a 3D or 4D volume of a target region, such as a fetal heart. The 3D or 4D volume of the heart may be used to determine a pump volume of the heart, diagnose structural heart defects, or access other desired diagnostic features of the heart. These diagnostic processes may be performed at the time of imaging. In other examples, the volume may be stored and the diagnostic processes may be performed at a time after the imaging. In particular, the image acquisition may be performed by a skilled ultrasound technician, while the diagnostic procedures may be performed by a physician that, while skilled in anatomy and diagnostics, may not be as skilled as the ultrasound technician in ultrasound imaging techniques.

In order to access desired slices of the volume for diagnostic or other purposes, or in order to perform the calculation of the pump volume, the volume representing the heart may first be aligned to a standard orientation. Alignment of the volume may be carried out by the technician, or by the physician or less skilled clinician. To ensure the standard alignment may be reached in an easy, fast, and reproducible manner, even if performed by a physician or other clinician not skilled in ultrasound techniques, the ultrasound system of FIG. 1 may include instructions executable to automatically or semi-automatically align the volume to the standard alignment based on a predetermined model representing the volume. The model may be compared to image data used to generate the volume, and adjusted until the model fits (e.g., matches) certain features of the image data (e.g., the size, position, and/or orientation of the model may be adjusted based on the image data). The adjusted model thus represents the size, shape, position, and orientation of the volume. The instructions may be further executable to determine the orientation of the volume by obtaining the orientation of the model. Once the orientation of the volume is determined, the volume may be automatically adjusted (e.g., rotated) until it reaches the standard alignment, at which point it may be saved for future processing and/or diagnostically relevant slices/images may be displayed.

FIG. 2 is a flow chart illustrating a method 200 for aligning a volume to a standard alignment according to an embodiment of the disclosure. Method 200 may be carried out according to instructions stored on a computing system, including but not limited to the processor and memory of the ultrasound system of FIG. 1. However, in other examples, method 200 may be carried out by a processor and memory of another suitable system, such as a computing system associated with a magnetic resonance imaging (MRI) system. Method 200 includes, at 202, acquiring a plurality of images with an ultrasound probe. The images may be acquired by a suitable probe in a suitable manner, such as a 2D or 3D probe, linear or array transducer probe, in a B-mode, according to a 3D-sweep acquisition or STIC acquisition mode, etc. In further examples, the plurality of images may alternatively or additionally be acquired with another imaging modality, such as MRI, PET-CT, or other imaging mechanism. At 204, method 200 includes constructing a three-dimensional or four-dimensional volume based on the plurality of images.

At 206, a volume model representing the 3D/4D volume is fit to the volume image data. Additional details regarding the fitting of the volume model to the volume will be presented below with respect to FIG. 3. Briefly, the fitting includes generating an initial volume model that has an initial scale and orientation based on a scale and orientation of the volume as input by a user, for example. After the initial model is generated, the model may be adjusted (e.g., size, position, orientation) until it matches the size, position, and orientation of the volume, as determined by the image data comprising the volume.

At 208, the volume is aligned to a standard orientation based on the volume model. Once the volume model is adjusted to fit the volume image data, the orientation of the model is determined by the computing system. Because the volume model corresponds to the generated volume, the orientation of the volume is assumed to be the same as the orientation of the model. Once the orientation of the volume is determined, the volume is aligned to a standard orientation by rotating or otherwise adjusting the volume. The standard orientation may be a suitable orientation in which the computing system may automatically obtain diagnostically relevant images, and may include certain features (e.g., heart chambers, valves, etc.) being represented in certain planes.

At 210, the aligned volume is stored, for example in the memory of the ultrasound system, for future processing. The future processing may include, as indicated at 212, retrieving diagnostically-relevant images, and/or measuring a volume and/or other diagnostically relevant features, as indicated at 214. In one example, the retrieved diagnostically-relevant images may be output for display on a display device.

Thus, the method described above acquires a plurality of images and constructs a three-dimensional or four-dimensional volume from the plurality of images. The volume is then aligned to a standard alignment by utilizing a model of the volume to determine the orientation of the volume. Each process described in the method above may be performed with a single ultrasound system in a single imaging session. However, in other examples, the image acquisition and volume construction may be performed by a first ultrasound system and the volume alignment and/or volume processing may be performed by a second, different ultrasound system. Further, in some examples the volume alignment may be performed by a suitable computing system not associated with the ultrasound image acquisition features of the ultrasound system (e.g., the transmitter/receiver).

An example method for fitting a dynamic model representing a heart to captured image data of a heart is presented below with respect to FIG. 3. Method 300 is one non-limiting example of how a volume model may be fit to volume data, as utilized in method 200 above. However, the methods described herein are not limited to alignment of a heart volume, as other volumes are possible. For example, a volume of a brain may be aligned to a suitable volume model of a brain. Method 300 may be performed by a computing system, such as a computing system of an ultrasound system (e.g., according to instructions stored on the memory of and executed by the processor of the ultrasound system of FIG. 1). Method 300 may be performed in order to align a three-dimensional volume of a heart constructed from a plurality of images acquired by the ultrasound system or other suitable imaging system, as described above with respect to FIG. 2.

Method 300 includes, at 302, obtaining an initial orientation and an initial scale of a volume representing the heart within a single plane of the volume. As explained above with respect to FIG. 2, a volume, such as a volume representing a heart, may be constructed from a plurality of frames of image data captured via ultrasound, for example. To determine the orientation of the volume, a volume model is fit to the image data of the volume. To expedite the fitting routine and increase the accuracy of the fitting, an initial scale and orientation of the volume may be obtained and subsequently used to generate an initial model of the volume. The initial scale and orientation of the volume may be obtained via user input in one example. The volume may be displayed to an operator, for example, in one or more planes, and the operator may adjust which planes of the volume are displayed. During display of the volume, the operator may input an indication of the initial scale and orientation of the volume, as indicated at 304. In examples where the volume includes a heart, the initial scale and orientation may be determined by the operator indicating the position and size of a sub-anatomical structure of the heart, such as the interventricular septum, for example by drawing a line along the septum. This line may be directional, for example, to indicate an up/down orientation of the volume. Additionally, the operator may provide an indication of a left/right orientation, for example by clicking on the left ventricle or other suitable landmark. The user input to the system may be provided to only one plane of the volume in order to minimize the amount of input, and hence skill, on the part of the operator. For example, the operator may indicate the position and size of the septum as well as up/down and left/right directionality of the volume to a four-chamber view of the heart in the A plane. However, in other examples, the initial scale and orientation may be identified automatically by the computing system or other system in communication with the computing system, via image recognition for example, as indicated at 306.

As used herein, the term "orientation" refers to the position of one or more structures of the volume relative to other structures within the volume with respect to the vertical, horizontal, and lateral axes of the transducer probe during the volumetric sweep of the transducer. For example, the orientation may be based on the relative position of the left and right ventricles, septum, apex, and/or crux with respect to the position of the ultrasound transducer during the volumetric sweep of the transducer, e.g., whether the left ventricle is positioned to the right or to the left of the right ventricle during the sweep, vertically above or vertically below the atria, whether the septum is positioned at an angle relative to vertical axis, or other suitable metric. While certain sub-structures of the volume may be used to define the orientation herein, it is to be understood that the entirety of the volume has the same orientation and that when the orientation of the volume is adjusted (e.g., rotated, angled, flipped, etc.), the entire volume is adjusted equally. Likewise, the term "scale" as used herein refers to a size of the entire volume relative to a minimum or maximum possible size of the volume, and when the scale is adjusted, the entire volume is increased or decreased in size equally across all aspects of the volume.

At 308, an initial volume model is built based on the initial orientation and scale determined above. The model may be generated offline, based on a plurality of images of the heart, for example, and may reflect a subset or all of the sub-anatomic features of the heart. In one example, the model may comprise a plurality of linked sub-models, where each sub-model represents a respective chamber of the heart. Each sub-model may have a predetermined size, shape, and position relative to the other sub-models, and thus adjustment to one of the sub-models may result in a corresponding adjustment to the remaining sub-models. Each sub-model may be deformable, such that the surface and hence volume of each sub-model may be adjustable.

Thus, building an initial model based on the initial scale and orientation includes building a volume model that includes a plurality of linked deformable sub-models, as indicated at 310. As used herein, "linked" indicates that certain parameters of each sub-model are set relative to the other sub-models. For example, each sub-model may be collectively scaled up or down in size according to a predetermined ratio. Further, if an adjustment is made to one sub-model, a corresponding adjustment is made to each other sub-model. Further still, a position of each sub-model may be set relative to a position of each other sub-model. Each deformable sub-model may represent a respective chamber of the heart, as indicated at 312.

At 314, the initial volume model is adjusted based on a comparison of the volume model to image data over time. This may include detecting an inner edge of a first chamber of the heart in the image data, as indicated at 316. In one example, the first chamber may be the left ventricle, but other chambers may be used. Further, in some examples an outer edge may be detected in addition or alternative to the inner edge. The entirety of the inner and/or outer edge may be detected, or a segment of the inner and/or outer edge may be detected. The At 318, the size, position, and/or orientation of a first sub-model representing the first chamber may be adjusted to align an edge of the first sub-model to the edge of the first chamber. This adjustment may be performed using a Kalman filter and may be based on previous frames of image data, as indicated at 320. The Kalman filter may make a prediction of where the edge of the first sub-model is to be positioned to align with the edge of the first chamber based on previous frames of image data (e.g., the Kalman filter tracks the edge of the first chamber over time), and then updates the prediction based on an error between the respective positions of the edge of the first sub-model and the edge of the first chamber of volume in the current frame of image data, for example. The remaining sub-models of the volume model may be adjusted based on the adjustment to the first sub-model, as indicated at 322. Thus, one sub-model of the plurality of linked sub-models may be analyzed and adjusted, with each other sub-model updated in correspondence to the adjustment to the one sub-model. In other examples, each sub-model may be compared a respective edge of a respective chamber and adjusted based on a respective error.

At 324, method 300 determines if a predetermined number of iterations of adjusting the volume model have been performed. For example, the volume model may be updated as described above for each of a plurality of sequential image frames, such as twenty frames or other suitable number of frames. If it is determined that the predetermined number of iterations of adjusting the model have not been performed, method 300 loops back to 314 to continue to adjust the model. If the predetermined number of iterations has been reached, method 300 proceeds to 326 to determine if a determined amount of error between the model and the image data is less than a threshold. In one example, the error may be the error between the edge of the first sub-model and the edge of the first chamber in the image data, as described above. The error may be determined for the last iteration of the adjustment performed, or it may be an average error of each error determined each time the model is adjusted. The threshold may be a suitable threshold, such as an amount of error that indicates the edges at least partially overlap.

Additionally, in some examples, the volume model may be a dynamic model that is configured to change size and/or shape over time, to reflect beating of the heart for example. Thus, the error being below the threshold may comprise the error for each of a plurality of frames of image data being below the threshold, even as the position of the edge of first chamber changes. Further, in some examples, after the predetermined number of iterations of the adjustment to the model have been performed, one or more rationality checks may be performed to ensure the model properly fits the image data. For example, once the model is fit to the image data and thus the orientation of the model is set, each sub-model may be assigned a respective chamber of the heart. The volume of each sub-model may be determined, and if the volumes of the sub-models corresponding to the atria are larger than the volumes of the sub-models corresponding to the ventricles, it may be determined that the model is flipped and hence does not accurately reflect the orientation of the volume.

If the error is less than the threshold, method 300 proceeds to 328 to indicate that the model fits the data, and then method 300 ends. If the error is not less than the threshold, or if the model does not pass the one or more rationality checks, method 300 proceeds to 330 to indicate an error may be present in the volume. For example, the image data used to generate the volume may be of low quality or otherwise degraded, and thus the automatic alignment of the model using the image data may not be accurate. In other examples, an anatomical abnormality may be present, thus confounding the fitting of the model to the volume. In such examples, the method may proceed back to the beginning and be repeated again, or the operator may be notified that the automatic alignment cannot be performed, and the operator may then manually align the volume, for example. Method 300 then ends.

Thus, methods 200 and 300 described above provide for an automated volume alignment where a volume representing an anatomical structure is automatically aligned according to a model of the volume. In one example, a user acquires a 4D sequence of the fetal heart, where the four chamber view is visible in the A-plane. The user then draws a line along the septum (from the apex to the crux, for example). This line yields information about the orientation of the heart and also about the scale/zoom factor of the ultrasound image. Additionally or alternatively, the user may place clicks on the landmarks, e.g. on apex and crux. Using this information as an initial starting point, a 3D dynamic heart model is automatically fit to the ultrasound data. The orientation of the ultrasound data may then be estimated based on the orientation of the heart model. The data is then rotated and scaled to a predefined standard orientation from which the standard planes can be generated.

The automatic or semi-automatic alignment routine described above includes adjusting a model of a volume representing an imaged structure (e.g., a model of a volume representing a heart as imaged by an ultrasound system) until the model fits image data used to generate the volume. However, in some examples, for an initial fit with respect to scale and orientation, the volume may be rotated and scaled to fit the model. After the initial fit, the volume may continue to be adjusted until it is determined the volume fits the model. Once the volume fits the model (e.g., selected edges of the volume align with selected edges of the model), the orientation of the model may be obtained and applied to adjust the orientation of the volume to the standard orientation. In examples where the scale of the model is adjusted to fit the model, once the orientation of the volume is determined, the scale may be re-adjusted so that the volume accurately reflects the scale of the structure being imaged. Additionally, in some examples, after the initial fit of the volume to the model, the model may be adjusted until it is determined the model fits the image data.

FIG. 4 is an example graphical user interface 400 that may be displayed by a computing system (e.g., the computing system of FIG. 1) to an operator during the execution of methods 200 and/or 300. As illustrated, interface 400 is displaying a four-chamber view of a volume representing a fetal heart in the A plane, where the volume is generated from ultrasound image data. A user has entered input to the interface to indicate the initial scale and orientation of the volume. For example, a line 402 has been entered along the interventricular septum. The line 402 is directional, and as such includes an arrow pointing toward the atria, in order to provide up/down orientation. Further, a dot 404 has been placed in the left ventricle, indicating the initial left/right orientation of the volume. While not shown in FIG. 4, in some examples, the computing system may be configured (e.g., include executable instructions) to output a notification to the operator to instruct the operator to place the indicators of the initial scale and orientation of the volume. As shown in FIG. 4, input is made to only one plane/view of the volume.

FIG. 5 is an example graphical user interface 500 that may be displayed by the computing system after the initial scale and orientation of the volume is obtained. Interface 500 includes the four-chamber view of the heart shown in FIG. 4, and also includes the volume model built based on the initial scale and orientation input as shown in FIG. 4. The volume model includes a plurality of linked sub-models each corresponding to a chamber of the heart, including a first sub-model 502, second sub-model 504, third sub-model 506, and fourth sub-model 508. While representations of the plurality of models are illustrated, it is to be understood that the models are for illustrative purposes and in some examples visual representations may not be displayed.

The initial volume model built based on the initial scale and orientation may not accurately fit the image data used to generate the volume. For example, as shown in FIG. 5, the size and orientation of the model does not match the size and orientation of the volume. Thus, as described above, the volume model may be adjusted based on the captured image data so the volume model matches the size and orientation of the volume. FIG. 6 is an example graphical user interface 600 showing the volume model after the size and orientation of the model is adjusted.

The technical effect of the disclosure may include an automatic or semi-automatic alignment of a three-dimensional or four-dimensional volume based on a deformable model representing the volume. Another technical effect of the disclosure may include the automatic acquisition of diagnostically-relevant images or the calculation of diagnostically relevant features of the aligned volume.

An embodiment relates to a method of aligning a volume constructed from captured image data to a standard orientation. The method includes determining an orientation and a scale of the volume based on a comparison of a volume model representing the volume to captured image data of the volume over time; and adjusting the volume according to the determined orientation and scale. In one example, determining the orientation and scale of the volume based on the comparison of the volume model to captured image data of the volume over time comprises receiving an identification of an initial orientation and an initial scale of the volume within a single plane of the volume, and fitting the volume model to the captured image data based on the initial orientation and initial scale of the volume. In an example, the volume is a four-dimensional volume representing a heart, and the volume model comprises a plurality of linked sub-models, each sub-model representing a respective chamber of the heart. In examples, receiving the identification of the initial orientation and the initial scale of the volume comprises receiving an identification of a position, size, and orientation of a selected sub-anatomical structure of the heart within the single plane of the heart and determining the initial orientation and the initial scale of the heart based on the identified position, size, and orientation of the selected sub-anatomical structure of the heart. In examples, the selected sub-anatomical structure of the heart comprises an interventricular septum. In one example, the identification of the position, size, and orientation of the selected sub-anatomical structure of the heart is received via user input, and the user input is received only at the single plane of the heart. In such examples, the user input used to determine the initial scale and orientation of the heart is only received at one plane and one view of the volume representing the heart, and not to any other planes or views of the volume. In other examples, the identification of the position, size, and orientation of the selected sub-anatomical structure of the heart is received via automatic image recognition performed on the captured image data. In examples, the method further comprises detecting an edge of a first chamber of the heart within the captured image data; adjusting a first sub-model of the plurality of linked sub-models based on an error between an edge of the first sub-model and the edge of the first chamber; and when the error is less than a threshold, indicating the first sub-model fits the captured image data. In some examples, the method further comprises adjusting each remaining sub-model of the plurality of linked sub-models based on the adjusting of the first sub-model. In examples, the volume model is a dynamic model configured to deform over time to reflect a change in chamber shape and size as the heart beats, and indicating the volume model fits the captured image data comprises indicating the volume model fits the captured image data when the edge of the first sub-model tracks the edge of the first chamber over time. In examples, adjusting the volume according to the determined orientation and scale comprises, after indicating the volume model fits the captured image data, adjusting an orientation of the volume to match the orientation of the volume model and outputting one or more standard planes of the volume for display on a display device.

Another embodiment of a method comprises accessing a four-dimensional volume representing a heart; and aligning the four-dimensional volume based on a dynamic volume model of the heart comprising a plurality of linked sub-models each representing a chamber of the heart. In examples, the four-dimensional volume is assembled from image data of the heart captured over time. In examples, aligning the four-dimensional volume based on the dynamic deformable model comprises generating an initial dynamic deformable model based on an initial orientation and scale of the four-dimensional volume identified based on user input to a single plane of the four-dimensional volume; and adjusting the initial dynamic deformable model to fit the image data. In examples, adjusting the initial dynamic deformable model to fit the image data comprises detecting an inner edge of a first chamber of the heart within the image data; and adjusting one or more of a size, position, and orientation of a first sub-model of the plurality of linked sub-models based on an error between an outer edge of the first sub-model and the inner edge of first chamber. In examples, the detecting the inner edge of the first chamber and the adjusting one or more of the size, position, and orientation of the first sub-model are performed for each of a plurality of frames of image data captured over time, and the method further comprises indicating the dynamic volume model fits the image data when an average of all errors determined for all frames is less than a threshold.

An embodiment relates to a system including an ultrasound probe to emit ultrasonic signals; an ultrasound receiver to receive echoes of the emitted ultrasonic signals; and a computing system operably connected to the ultrasound probe, ultrasound receiver, and a display device, the computing system including instructions to: acquire a plurality of images of an anatomical structure via a volumetric sweep of the ultrasound probe; reconstruct the plurality of images into a four-dimensional volume; and align the four-dimensional volume with respect to a dynamic volume model of the four-dimensional volume. In examples, to align the four-dimensional volume with respect to the dynamic volume model, the computing system includes instructions to adjust the dynamic volume model to fit image data obtained from the plurality of images of the anatomical structure; determine an orientation of the four-dimensional volume based on an orientation of the adjusted dynamic volume model; and align the four-dimensional volume to a standard orientation. In examples, the computing system includes further instructions to output one or more slices of the four-dimensional volume for display on the display device; receive user input indicating an initial scale and orientation of the four-dimensional volume; and build an initial dynamic volume model based on the initial scale and orientation of the four-dimensional volume, where the instructions to adjust the dynamic volume model to fit the image data include instructions to adjust the initial dynamic volume model. In examples, the computing system includes further instructions to, after aligning the four-dimensional volume with respect to the dynamic volume model, obtain one or more slices of the four-dimensional volume for display on the display device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal language of the claims.

The invention claimed is:

1. A method of aligning a volume constructed from captured image data to a standard orientation, comprising:
displaying an image based on the captured image data;

receiving identification of an anatomical feature in the image via a user input;

determining an initial orientation and scale of the volume based on the identification of the anatomical feature;

fitting a volume model to the volume based at least in part on the initial orientation and scale of the volume;

determining an updated orientation and scale of the volume based on the volume model after said fitting the volume model to the volume; and adjusting the volume to the standard orientation based on the determined updated orientation and scale.

2. The method of claim 1, wherein determining the initial orientation and scale of the volume comprises receiving an identification of the initial orientation and scale of the volume within a single plane of the volume.

3. The method of claim 2, wherein the volume is a four-dimensional volume representing a heart, and wherein the volume model comprises a plurality of linked sub-models, each sub-model representing a respective chamber of the heart.

4. The method of claim 3, wherein receiving the identification of the anatomical feature comprises receiving an identification of a position, size, and orientation of a selected sub-anatomical structure of the heart within the single plane of the heart and determining the initial orientation and the initial scale of the heart based on the identified position, size, and orientation of the selected sub-anatomical structure of the heart.

5. The method of claim 4, wherein the selected sub-anatomical structure of the heart comprises an interventricular septum and wherein the user input includes a line drawn along the interventricular septum.

6. The method of claim 4, wherein the identification of the position, size, and orientation of the selected sub-anatomical structure of the heart is received via the user input.

7. The method of claim 6, wherein the user input is received only at the single plane of the heart.

8. The method of claim 4, wherein the identification of the position, size, and orientation of the selected sub-anatomical structure of the heart is received via automatic image recognition.

9. The method of claim 4, further comprising:

detecting an edge of a first chamber of the heart within the captured image data;

adjusting a first sub-model of the plurality of linked sub-models based on an error between respective positions of an edge of the first sub-model and the edge of the first chamber; and when the error is less than a threshold, indicating the first sub-model fits the captured image data.

10. The method of claim 9, further comprising adjusting each remaining sub-model of the plurality of linked sub-models based on the adjusting of the first sub-model.

11. The method of claim 10, wherein the volume model is a model of the heart and each of the plurality of linked sub-models represents a respective chamber of the heart.

12. The method of claim 11, further comprising adjusting one of the plurality of sub-models, analyzing the one of the plurality of sub-models after said adjusting the one of the plurality of sub-models, and updating another of the plurality of sub-models in correspondence to said adjusting the one of the plurality of sub-models.

13. The method of claim 9, wherein the volume model is a dynamic model configured to deform over time to reflect a change in chamber shape and size as the heart beats, and wherein indicating the volume model fits the captured image data comprises indicating the volume model fits the captured image data when the edge of the first sub-model tracks the edge of the first chamber over time.

14. The method of claim 1, wherein said user input comprises a line drawn along the anatomical feature.

15. The method of claim 14, further comprising displaying the line on the image.

16. The method of claim 14, wherein the line is directional.

17. The method of claim 16, further comprising displaying the line that includes an arrow to indicate a direction.

18. The method of claim 1, further comprising receiving identification of a second anatomical feature in the image via a second user input comprising a dot placed in the second anatomical feature.

19. The method of claim 18, wherein the second anatomical feature is a left ventricle.

20. The method of claim 1, further comprising receiving an indication of at least one of a left and a right orientation in the image via the user input.

21. A method, comprising:

accessing a four-dimensional volume representing a heart; and aligning the four-dimensional volume based on a dynamic volume model of the heart comprising a plurality of linked sub-models each representing a chamber of the heart.

22. The method of claim 21, wherein the four-dimensional volume is assembled from image data of the heart captured over time, and wherein aligning the four-dimensional volume based on the dynamic volume model comprises:

generating an initial dynamic deformable model based on an initial orientation and scale of the four-dimensional volume identified based on user input to a single plane of the four-dimensional volume; and adjusting the initial dynamic deformable model to fit the image data.

23. The method of claim 22, wherein adjusting the initial dynamic deformable model to fit the image data comprises:

detecting an inner edge of a first chamber of the heart within the image data; and adjusting one or more of a size, position, and orientation of a first sub-model of the plurality of linked sub-models based on an error between respective positions of an outer edge of the first sub-model and the inner edge of first chamber.

24. The method of claim 23, wherein the detecting the inner edge of the first chamber and the adjusting one or more of the size, position, and orientation of the first sub-model are performed for each of a plurality of frames of image data captured over time, and further comprising indicating the dynamic volume model fits the image data when an average of all errors determined for all frames is less than a threshold.

25. A system, comprising:

an ultrasound probe to emit ultrasonic signals;

an ultrasound receiver to receive echoes of the emitted ultrasonic signals; and a computing system operably connected to the ultrasound probe, the ultrasound receiver, and a display device, the computing system including instructions to:

acquire a plurality of images of an anatomical structure via a volumetric sweep of the ultrasound probe;

reconstruct the plurality of images into a four-dimensional volume;

receive identification of an anatomical feature of the four-dimensional volume via a user input;

determine an initial orientation and scale of the four-dimensional volume based on the identification of the anatomical feature;

fit a dynamic volume model of the four-dimensional volume to the four-dimensional volume based at least in part on the initial orientation and scale of the four-dimensional volume;

determine an updated orientation and scale of the four-dimensional volume after said fitting the dynamic volume model to the four-dimensional volume, based on an orientation and scale of the dynamic volume model; and align the four-dimensional volume to a standard orientation based on the determined updated orientation and scale of the four-dimensional volume.

26. The system of claim 25, wherein the user input includes one or more of a line drawn along the anatomical feature and a dot placed in the anatomical feature or a second anatomical feature to indicate a left/right orientation.

27. The system of claim 25, wherein the computing system includes further instructions to:

output one or more slices of the four-dimensional volume for display on the display device;

receive the user input indicating the initial scale and orientation of the four-dimensional volume; and build an initial dynamic volume model based on the initial scale and orientation of the four-dimensional volume, where the instructions to fit the dynamic volume model to the four-dimensional volume include instructions to adjust a size, position, and/or orientation of the initial dynamic volume model.

28. The system of claim 25, wherein the computing system includes further instructions to, after aligning the four-dimensional volume to the standard orientation, obtain one or more slices of the four-dimensional volume for display on the display device.

* * * * *